United States Patent [19]

Miller et al.

[11] Patent Number: 5,575,293

[45] Date of Patent: Nov. 19, 1996

[54] APPARATUS FOR COLLECTING AND STAGING TISSUE

[75] Inventors: Michael E. Miller; Joseph L. Mark, both of Indianapolis, Ind.; Alan M. Schechter, Long Beach, Calif.

[73] Assignee: Promex, Inc., Indianapolis, Ind.

[21] Appl. No.: 383,777

[22] Filed: Feb. 6, 1995

[51] Int. Cl.⁶ .................................................... A61B 10/00
[52] U.S. Cl. ........................... 128/752; 128/758; 604/319
[58] Field of Search .................................. 128/744, 752, 128/753, 758; 604/317, 319; 606/115, 170

[56] References Cited

U.S. PATENT DOCUMENTS

| | | |
|---|---|---|
| 3,224,434 | 12/1965 | Molomut et al. |
| 3,661,114 | 5/1972 | Jensen et al. |
| 3,889,657 | 6/1975 | Baumgarten . |
| 3,929,133 | 12/1975 | Ragab . |
| 4,393,879 | 7/1983 | Milgrom ................................ 128/758 |
| 4,643,197 | 2/1987 | Greene et al. ......................... 128/762 |
| 5,037,379 | 8/1991 | Clayman et al. ....................... 600/37 |
| 5,108,381 | 4/1992 | Kolozsi .................................. 604/319 |
| 5,197,968 | 3/1993 | Clement ................................ 606/115 |
| 5,269,785 | 12/1993 | Bonutti ................................... 606/80 |
| 5,275,609 | 1/1994 | Pingleton et al. .................... 606/170 |
| 5,290,249 | 3/1994 | Foster et al. .......................... 604/174 |
| 5,290,303 | 3/1994 | Pingleton et al. ...................... 606/70 |

OTHER PUBLICATIONS

Lobe TE, Schropp KP, Joyce P, Lasater O, Jenkins J, "The Suiteability of Automatic Tissue Morcellation for the Endoscopic Removal of Large Specimens in Pediatric Surgery", *Pediatr Surg* 29:232–234, 1994.

*Primary Examiner*—Max Hindenburg
*Attorney, Agent, or Firm*—Woodard, Emhardt, Naughton, Moriarty & McNett

[57] ABSTRACT

A tissue collecting and staging apparatus is operable with a minimally invasive percutaneous tissue removal system to collect a mass of tissue bits and provide an ordered, or staged, version of the bulk tissue prior to removal. The apparatus includes a chamber under vacuum and at least one tube having a first end extending into the chamber for receiving tissue bits therein. A tissue collection container is slidably disposed over the first tube end and extends along a portion of the tube within the chamber. As tissue bits are dispensed from the tube into the tissue collection container, the vacuum draws the container away from the first tube end to maintain vacuum within the tube. The resulting collected tissue mass is a staged reconstruction of the bulk tissue prior to removal to facilitate analysis of the tissue by a pathologist.

24 Claims, 3 Drawing Sheets

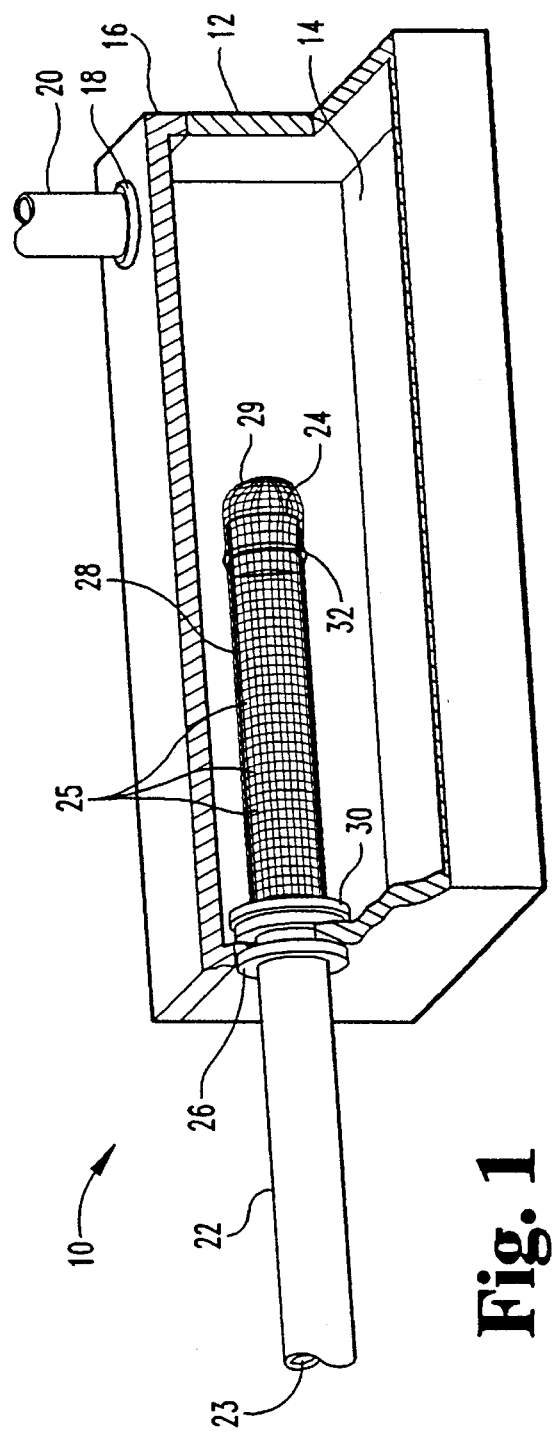
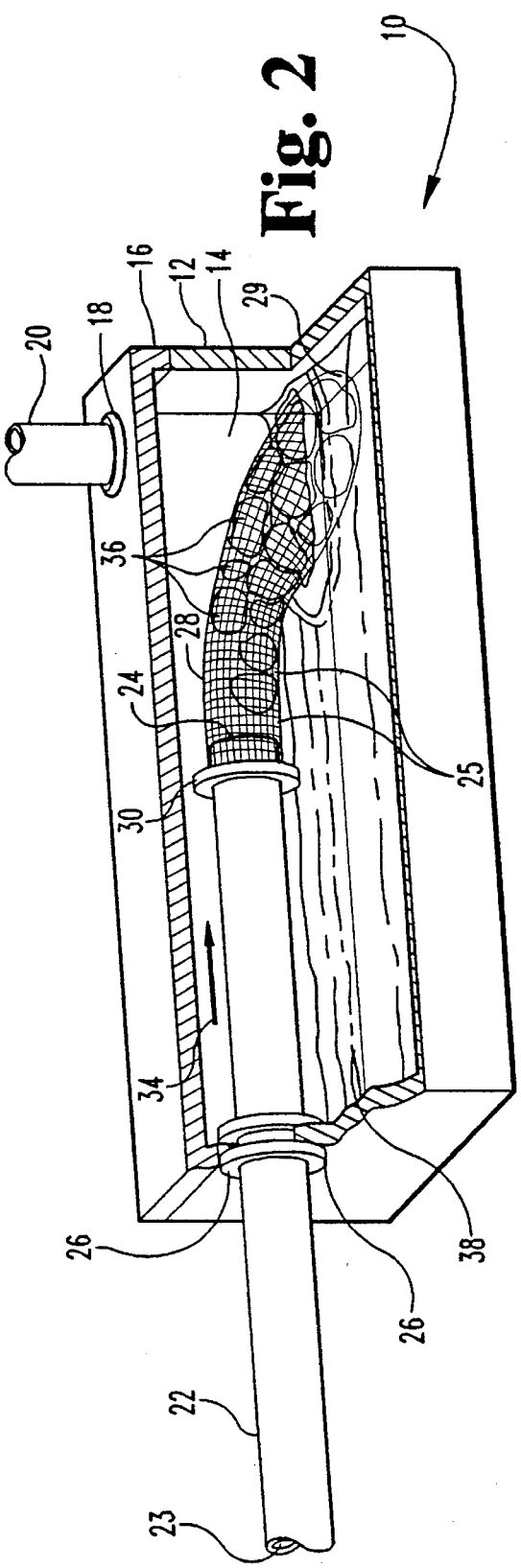

APPARATUS FOR COLLECTING AND STAGING TISSUE

FIELD OF THE INVENTION

This invention relates in general to minimally invasive tissue removal systems and more specifically to apparata for collecting and staging tissue removed via a percutaneously inserted tissue cutting tool.

BACKGROUND OF THE INVENTION

In the past several years, minimally invasive surgical techniques have been developed to, inter alia, reduce trauma to surrounding tissue and promote faster healing periods. Percutaneous instrumentation is now widely available to effectuate the removal of bodily organs, degenerated tissue, excess tissue and the like. Usually, a cutting instrument is attached to, or comprises, the end of a cannula for excising the tissue. A vacuum source is then typically employed for removing the excised tissue through the cannula.

Various devices and methods have been developed for collecting excised tissue. In particular, U.S. Pat. No. 5,037,379 to Clayman et al. discloses a surgical tissue bag which is percutaneously inserted to receive a tissue mass therein. A tissue morcellator is then introduced into the bag for debulking the tissue mass. The debulked tissue mass within the tissue bag is then removed through the insertion site.

U.S. Pat. Nos. 3,224,434, 3,661,144, 3,889,657, 3,929,133, 4,393,879, 5,108,381 and 5,197,968 disclose tissue removal systems wherein a stationary and/or rigid tissue collection trap is used to collect the tissue samples therein. Some of the systems provide removable traps for accessing the collected tissue while others do not. In each case, however, the tissue collection trap or container is of a predetermined size and remains stationary within the system for the duration of the tissue collection procedure.

An important aspect of any tissue removal procedure is the subsequent pathological evaluation of the removed tissue. This is particularly critical when removing, for example, cancerous or diseased tissue. Prior art systems, while permitting complete removal and collection of tissue, are not able to insure the staging, or ordering, of collected tissue. Thus, it is usually extremely difficult, and often impossible, for a pathologist to reconstruct the bulk tissue, as it existed prior to removal, from the mass of tissue bits provided by such systems. What is needed is a tissue collection and staging apparatus which provides a mass of collected tissue bits in substantially the same order in which they were excised from the bulk tissue. Such an apparatus would alleviate the often insurmountable burden on the pathologist to attempt to reconstruct the bulk tissue from the collected tissue bits.

SUMMARY OF THE INVENTION

In order to address the foregoing shortcomings of the prior art, a tissue collection and staging apparatus is disclosed herein which permits the ordered collection of tissue bits. Such an apparatus obviates the need to reconstruct the bulk tissue from a mass of randomly arranged tissue bits.

According to one aspect of the present invention, an apparatus for collecting and staging tissue bits comprises a chamber having a first port connected to a source of vacuum, an elongated tube defining a channel therethrough for receiving the tissue bits and means for collecting the tissue bits. The tube has a first end extending into the chamber in a first direction and the collecting means is slidably disposed over a portion of the tube within the chamber including the first end. The collecting means is configured to retain the tissue bits therein yet permit the vacuum source to create a vacuum within the channel. The vacuum draws the tissue bits through the channel and into the collecting means, and further draws the collecting means away from the tube in the first direction as the tissue bits collect within the collecting means. Such action permits the vacuum source to maintain the vacuum within the channel and results in the tissue bits being staged within the collecting means in substantially the order in which they entered the channel.

According to another aspect of the present invention, an apparatus for collecting and staging tissue bits comprises a chamber having a cover, the cover having a first surface facing the chamber, a first port connected to a source of vacuum and a second port for receiving the tissue bits, and a tissue collection member disposed between the chamber and the cover. The tissue collection member, chamber and cover are configured to permit relative rotation between the tissue collection member and either the chamber or cover. The tissue collection member includes a third port axially aligned with the first port, wherein the cover, tissue collection member and chamber are in a sealing arrangement so that the vacuum source creates a vacuum within the chamber through the axially aligned first and third ports. The tissue collection member further includes a number of elongated tubes each defining a channel therethrough for receiving tissue bits, each of the number of tubes having a first end extending into the chamber in a first direction and a second end coterminous with the first surface of the cover. Finally, the tissue collection member includes a tissue collection container slidably disposed over the first end, and extending along a portion, of at least one of the tubes for collecting tissue bits. The tissue collection container has apertures sized to retain the tissue bits therein yet permit the vacuum source to create a vacuum within the channel of the tube. The rotation of the tissue collection member relative to one of the cover and like chamber axially aligns the second port with the second end of one of the elongated tubes so that the vacuum draws the tissue bits through the second pork, through the axially aligned tube and into the tissue collection container. The vacuum further draws the collection container away from the tube in the first direction as the tissue bits collect within the collection container to thereby permit the vacuum source to maintain the vacuum within the channel, whereby the tissue bits are staged within the collection container in substantially the order in which they entered the channel.

According to a further aspect of the present invention, the combination of a tissue morcellator for percutaneous tissue removal and an apparatus for collecting and staging morcellated tissue bits from the morcellator is provided. The apparatus comprises a chamber having a first port connected to a source of vacuum, an elongated tube defining a channel therethrough for receiving the tissue bits, the tube having a first end extending into the chamber in a first direction, and a tissue collection container slidably disposed over the first end of the tube and extend along a portion thereof. The tissue collection container has apertures sized retain the tissue bits therein yet permit the vacuum source to create a vacuum within the channel of the tube. The vacuum draws the tissue bits through the channel and into the collecting means, and the vacuum further draws the collecting means away from the tube in the first direction as the tissue bits collect within the collecting means to thereby permit the vacuum source to maintain the vacuum within the channel. Thus, the morcellated tissue bits are staged within the collecting means in substantially the order in which they were morcellated.

It is one object of the present invention to provide a tissue collection and staging apparatus which collects tissue bits in substantially the order in which they were received by the apparatus.

It is another object of the present invention to provide a tissue collection and staging apparatus wherein a plurality of tissue collection means are provided for collecting and staging tissue.

These and other objects of the present invention will become more apparent from the following description of the preferred embodiment.

BRIEF DESCRIPTION OF THE DRAWINGS

FIG. 1 is a side elevational view with a partial cutaway showing a preferred embodiment of an apparatus for collecting and staging tissue in accordance with the present invention.

FIG. 2 is a side elevational view with a partial cutaway showing the embodiment of FIG. 1 with tissue bits collected therein.

DESCRIPTION OF THE PREFERRED EMBODIMENT

Figure 4:
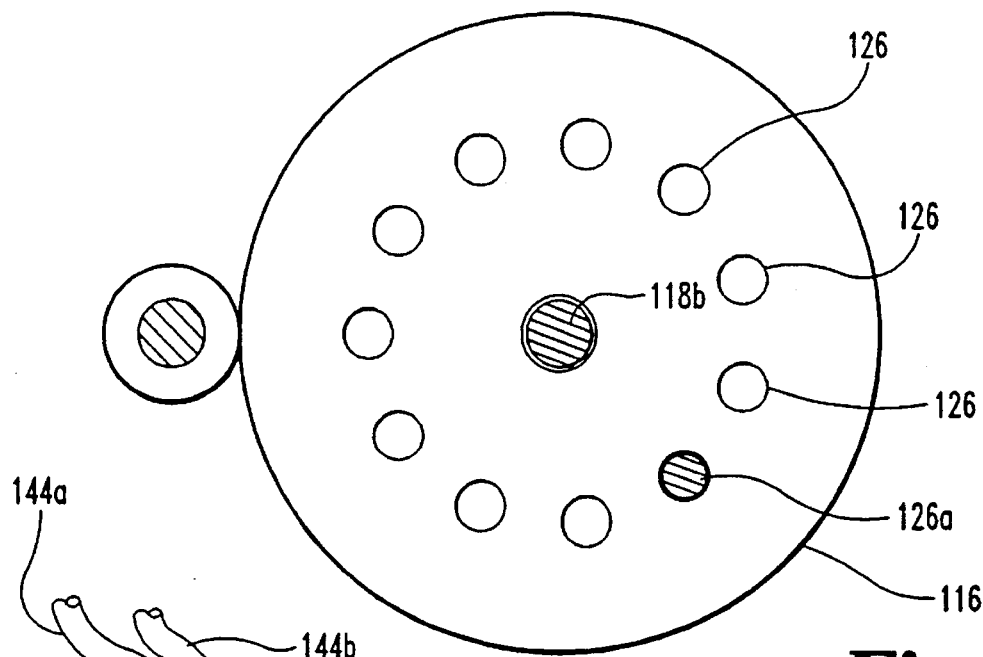
FIG. 4 is a top plan view of the embodiment shown in FIG. 3 along the section lines 4—4.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In accordance with the present invention, an apparatus for collecting and staging tissue is shown in FIGS. 1–4. Such an apparatus has application, for example, in a system for percutaneous removal of tissue, such as the system shown in FIG. 5. The apparatus receives tissue bits provided by a tissue cutting tool, or morcellator, and provides an ordered, or staged, version of the removed tissue. In other words, tissue is collected by the apparatus of the present invention in the order in which it was excised by the tissue morcellator so that the resulting collected tissue mass replicates the tissue as it existed prior to removal. This feature greatly enhances post operative pathological examination of percutaneously removed tissue.

According to a preferred embodiment of a tissue collecting and staging apparatus 10 of the present invention, as illustrated in FIGS. 1 and 2, a housing 12 is provided which includes a lid 16. The lid 16 and housing 12 are designed to be sealingly engaged during operation of the apparatus 10, and together define a chamber 14 therein. Lid 16 has a port 18 therethrough which is connected via tube 20 to a source of vacuum (not shown). Although the lid 16 provides a convenient location for port 18, the present invention contemplates locating port 18 and tube 20 at any other convenient location through the housing 12. Moreover, although the port 18 and tube 20 may be sealingly engaged as shown in FIGS. 1 and 2, these two elements may be combined into a port/tube of unitary construction.

The housing 12 further includes a port 26 therethrough connected to a tissue receiving tube 22. As with the vacuum port 18, port 26 may be disposed at any convenient location through the housing 12 or lid 16. Moreover, the tube 22 and port 26 combination may be of unitary construction.

A portion of tube 22 extends into the chamber 14 and terminates at a tissue dispensing end 24. The tube 22 has a channel 23 for receiving and transporting tissue bits to be collected by the apparatus 10. Although the cross-section of the channel 23 is circular in a preferred embodiment, the invention contemplates channel 23 cross-sections having a variety of shapes including, for example, oval, D-shaped, square, or star-shaped to name a few. The importance of channel 23 lies in its ability to transport tissue past the end 24 of tube 22 and not in a particular geometric shape.

Disposed over the end 24 of the tube 22 and extending along a portion of tube 22 within the chamber 14 is a tissue collection container 28. Container 28 is attached at its open end to a sealing ring 30 which is slidably disposed about the outer surface of the tube 22. A flange 32 is included on outer surface of the tube 22 adjacent the tube end 24 and provides a stop for the sealing ring 30 (and tissue collection container 28) moving in the direction of arrow 34.

Although many types of materials may be used for the tissue collection container 28, a flexible nylon mesh bag is used in a preferred embodiment. In other contemplated embodiments, the container 28 may be rigid or flexible, slotted, and/or perforated, and constructed of metallic, synthetic, cloth, biological, dissolving or other types of materials, all depending on the requirements and preference of a particular user. In one embodiment, an important requirement in the structure and construction of container 28 is that it must allow vacuum from tube 20 to be created within the channel 23 of tube 22. This requirement is preferably accomplished with a flexible nylon mesh bag having apertures of a predetermined size disposed therethrough. The apertures 25 are small enough to retain tissue bits 36 therein, yet large enough ho permit vacuum from tube 20 to be created within the channel 23 of tube 22. Apertures 25 meeting these two requirements further allows fluid 38 accompanying the tissue bits to flow through the apertures 25 and into the chamber 14.

A variety of structures and materials may similarly be used for the sealing ring 30; an important requirement being that the ring 30 be freely slidable along the exterior surface of the tube 22 in a manner to be described hereinafter. In a preferred embodiment, sealing ring 30 is made of rubber or a flexible polymer such as nylon, plastic, or the like, although the present invention contemplates other materials for sealing ring 30 having elastic qualities.

The flange 32 extends radially away from the outer surface of the tube 22 sufficiently to stop the sealing ring 30, sliding in the direction of arrow 34, from sliding off the end 24 of the tube 22. However, since it is contemplated that a new tissue collection container 28 will be used for each tissue collection procedure, the flange 32 must be sized to permit the sealing ring 30 (and tissue collection container 28) to be loaded onto, and removed from, tube 22. The use of such a flange 32 requires the sealing ring 30 to have an elastic quality that permits it to be temporarily deformed while loading a new tissue collection container 28 onto the tissue receiving tube 22. The sealing ring must then constrict to allow a sealing, yet sliding, relationship with the outer surface of the tube 22. In an alternate embodiment (not shown), the flange mechanism is provided on a threaded or pressure fitting tube extension which has an outer diameter larger than that of tube 22. In this case, the sealing ring 30 need not be flexible enough to stretch over the flange mechanism since the sealing ring 30/tissue collection container 28 may be loaded and unloaded onto tube 22 while the tube extension is disengaged from the tube 22. In such an embodiment, the sealing ring 30 need not be flexible and may be of metallic, rigid plastic or polymer, wood or other rigid material construction.

The operation of a tissue collection and staging apparatus 10 will now be explained with reference to FIGS. 1 and 2. With the cover 16 of the housing 12 removed, a tissue collection container 28 is loaded onto the portion of the tube 22 extending into the chamber 14 as shown in FIG. 1. With the lid 16 hermetically sealed to the housing 12, vacuum from a vacuum source (not shown) is created within tube 20. Since the chamber 14 is vacuum-tight, the vacuum within tube 20 will be created within the chamber 14 and within the channel 23 of tube 24. Tissue bits entering the channel 23 of tube 22 under the force of the vacuum created therein will begin filling the bottom portion 29 of the tissue collection container 28 in the order in which they entered channel 23. As the tissue bits 36 begin to form a mass within the bottom portion 29 of the tissue collection container 28, the vacuum created within chamber 14 begins to slide the tissue collection container 28 and sealing ring 30 in the direction of arrow 34 as shown in FIG. 2. This sliding action causes the mass of tissue bits 36 contained in the bottom portion 29 of the tissue collection container 28 to slide away from the tube opening 24, thereby allowing the vacuum created within tube 20 to be maintained within channel 23 through open apertures 25 of the container 28. As more tissue bits 36 flow into the tissue collection container 28, the container 28 and seal ring 30 continue to move in the direction of arrow 34 so that new apertures 25 become available between the end 24 of tube 22 and the mass of tissue bits 36 so that a continuous vacuum can be maintained within channel 23. When the sealing ring 30 eventually slides into contact with flange 32, the movement of the container 28 in the direction of arrow 34 will cease and the tissue bits 36 entering the container 28 will eventually clog the remaining apertures 25 between the end 24 of the tube 22 and the mass of tissue bits 36 contained within the container 28. When the container 28 has been completely filled with tissue bits 36, most or all of the apertures 25 in the vicinity of the end 24 of the tube 22 will be clogged with tissue bits, thereby causing the vacuum created within channel 23 of tube 22 to cease. The housing 12 and/or lid 16 may be made transparent to provide the apparatus 10 operator with a visual indication that the container 28 is full, or known vacuum sensing means may be used to signal such a condition to the operator.

Due to the manner in which the tissue bits 36 entered the container 28 as just described, the resulting mass of tissue bits 36 constitutes a staged version of the original tissue mass. In other words, the resulting filled container 28 contains an ordered mass of tissue bits 36. The size of the tissue collection container 28 may be varied to correspond to the approximate size of the tissue mass being collected. In this way, tissue masses can be ordered, or staged, for subsequent pathological examination.

Figure 3:
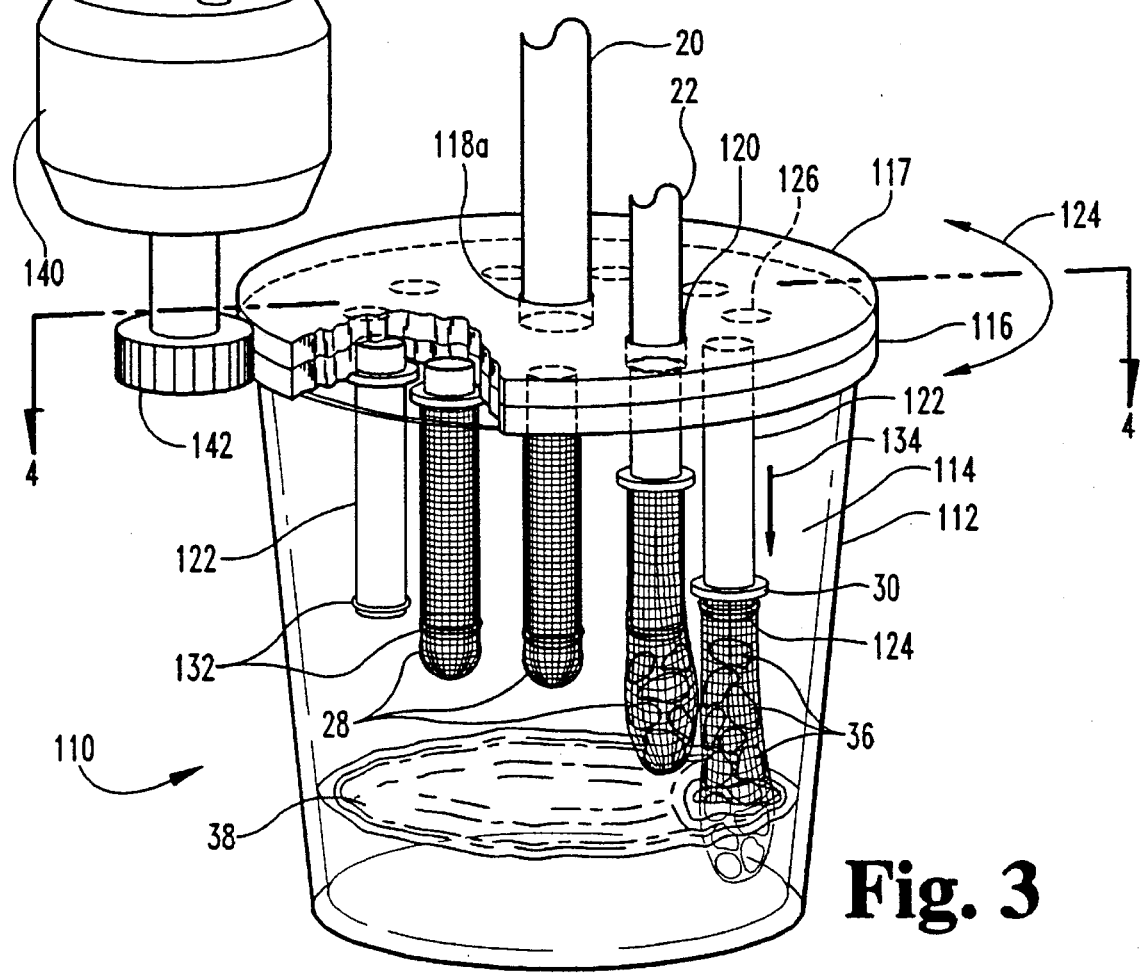
FIG. 3 is a side elevational view with a partial cutaway showing an alternate embodiment of an apparatus for collecting and staging tissue in accordance with the present invention.

Referring now to FIGS. 3 and 4, an alternate embodiment of a tissue collecting and staging apparatus 110 is shown. In operation, tissue collecting and staging apparatus 110 cooperates with tissue collection container 28 in a manner identically to that described in the previous embodiment. Identical numbers are therefore shown in FIGS. 3 and 4 which correspond to identical structural components of FIGS. 1 and 2.

Referring to FIG. 3, the tissue collecting and staging apparatus 110 includes a container 112, a tissue collection member 116, and a cover 117. The member 116 and cover 117 are rotatable relative to each other in the directions of the double-headed arrow 124. In one embodiment, member 116 is rotatable while the container 112 and cover 117 remain stationary. In an alternative embodiment, the cover 117 is rotatable in the directions of arrow 124 while the member 116 and container 112 remain stationary. In either case, an electrical motor 140 is connected to a power source (not shown) via electrical conductors 144a and 144b, and includes a drive gear 142 operatively engaged with one of the member 116 and cover 117 to provide the respective rotation.

Cover 117 includes a vacuum port 118a which is connectable to vacuum tube 20 and a tissue collection port 120 for connection to a tissue collection tube 22. In either case, the respective port and tube may be of unitary construction.

Referring to FIG. 4, member 116 has a vacuum pork 118b disposed therethrough. As shown in FIG. 3, vacuum ports 118a and 118b are axially aligned so that when member 116 and cover 117 are juxtaposed in operable relationship, vacuum created within tube 20 is transferred to chamber 114. Tube 20 may terminate coextensive with port 118b or, alternatively, may extend substantially into the chamber 114. A series of tissue collection ports 126 are radially disposed about the vacuum port 118b of member 116. Extending downwardly into the chamber 114 from each of the tissue collection ports 126 is a tube 122 having a tissue dispensing end 124 and a flange 132 adjacent end 124. Each of the tubes 122 are structurally identical to the tube 22 described with respect to the previous embodiment.

In the operation of one embodiment, the electric motor 140 causes member 116 to be rotated relative to the cover 117 in either of the directions shown by arrow 124 until the tissue collection port 120 of cover 117 is axially aligned with one of the tissue collection ports 126 of the member 116. FIGS. 3 and 4 show the tissue collection port 120 being axially aligned with the tissue collection port 126a. With the tissue collection ports 120 and 126a so aligned, tissue bits 36 are collected and staged within a tissue collection container 28 as previously described. When a tissue collection container 28 is full, or contains a desired amount of tissue bits, the motor 140 is actuated so that tissue collection port 120 of cover 117 becomes aligned with another tissue collection port 126, wherein a new tissue collection container 28 can be filled with tissue bits 36. In this way, a surgeon can collect numerous tissue samples without having to stop the procedure to provide a new tissue collection container 28.

Although the tissue collecting and staging apparatus 110 is shown in FIGS. 3 and 4 as having ten tubes 122 (corresponding to ten tissue collection containers 28), the present invention contemplates using as few as two tubes 122 and as many as practicable with the vacuum source being used. In other words, the upper limit on the number of tubes 122 that can be included within the tissue collecting and staging apparatus 110 is determined by the ability of the vacuum source to create a sufficient vacuum within the chamber 114 and within the tubes 122 to permit the collection and staging of tissue bits 36 within the tissue collection containers 28.

Figure 5:
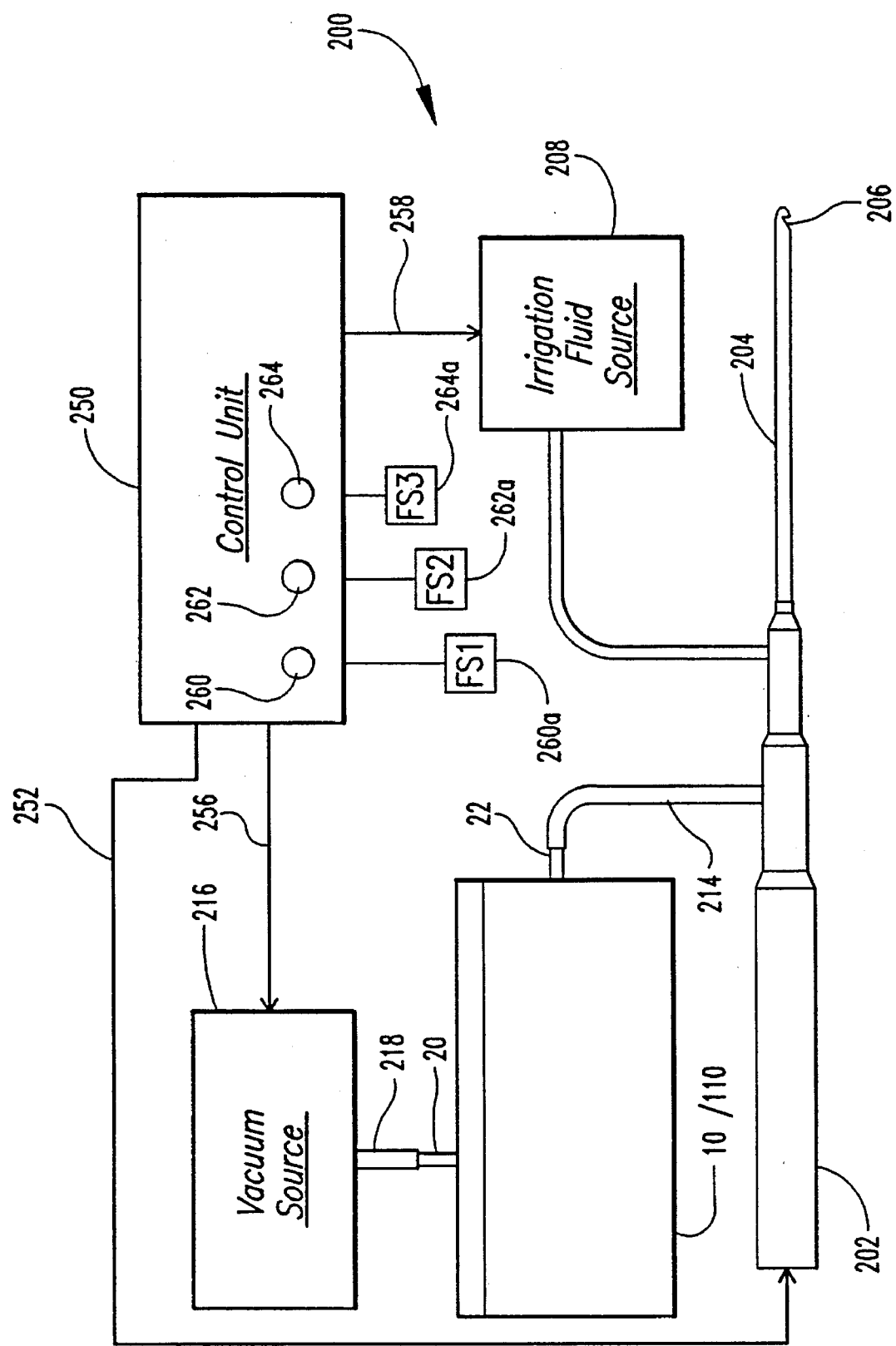
FIG. 5 is a diagrammatic view of a typical system for minimally invasive tissue removal in which an apparatus for collecting and staging tissue, in accordance with the present invention, may be used.

Referring now to FIG. 5, a typical tissue removal system 200 to be used with the tissue collection and staging apparatus 10 or 110 of the present invention is shown. A tissue cutting tool, or morcellator, 202 includes a cannula 204 and a cutting end 206 which is adapted to be percutaneously introduced at the site of the tissue removal. Such a tissue cutting tool 202 is percutaneously insertable into a variety of body locations to effectuate the removal of tumors, cysts, degenerated tissue, and the like. The tissue cutting tool 202 includes an irrigation line 212 and an aspiration line 214 extending therefrom. The two lines are used to provide irrigation fluid and aspiration vacuum at the cutting end 206 of the disposable tissue cutting tool 202.

Irrigation line 212 is connected to a source of irrigation fluid 208. Such an irrigation fluid source 208 would typically include a balanced sterile saline solution (BSS), which is fed into the disposable tissue cutter 202 to pass to the cutting end 206. In an alternate embodiment, the irrigation fluid source can be replaced by an insuflation gas source when necessary to inflate and maintain the working site.

The system 200 further includes a tissue collecting and staging apparatus 10 or 110, corresponding to one of the two embodiments of the invention disclosed herein. FIG. 5 shows the embodiment 10 of FIGS. 1 and 2 connected to the system 200. The tissue receiving tube 22 of the apparatus 10 is connected to the aspiration line 214. Vacuum tube 20 of tissue collecting and staging apparatus 10 is connected to a vacuum source 216 via a vacuum line 218.

The operation of the interrelated components of the system 200 is controlled by a control unit 250. Control unit 250 supplies electrical signals to the tissue morcellator 202 via the signal line 252. Similarly, the control unit 250 supplies electrical signals to the vacuum source 215 via the signal line 256 and to the irrigation fluid source 208 via signal line 258. The various parameters of the system 200 components, such as cutter speed, fluid pressure, and vacuum level may be set by actuating control knobs 260, 262, and 264. Moreover, the actuation of the various system components may be controlled via a series of foot switches 260a, 262a, and 264a. For example, the operation of the tissue morcellator 202 may be actuated by depressing foot switch 260a, and the vacuum source 216 and fluid source 208 may be actuated by depressing foot switches 262a and 264a, respectively.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for collecting and staging tissue bits excised from a patient comprising:

an elongated tube defining a channel therethrough for receiving the excised tissue bits; and a collection container slidably disposed over a portion of said tube for collecting the excised tissue bits;

wherein said collection container is drawn away from said tube as it receives the excised tissue bits therein, whereby the tissue bits are staged within said collection container in substantially the order in which they entered said channel.

2. The apparatus of claim 1 further including:

a chamber, wherein said elongated tube has a first end extending into said chamber, and said collection container is slidably disposed over a portion of said tube adjacent said first end.

3. The apparatus of claim 2 wherein said chamber further includes a first port connected to a source of vacuum for generating a vacuum in said chamber.

4. The apparatus of claim 3 wherein said collection container is configured to permit communication of a vacuum within said chamber with said channel, wherein the vacuum draws said collection container away from said tube as the container receives the tissue bits therein.

5. An apparatus for collecting and staging tissue bits excised from a patient comprising:

a chamber having a first port connected to a source of vacuum for generating a vacuum in said chamber;

an elongated tube defining a channel therethrough for receiving the excised tissue bits, said tube having a first end extending into said chamber in a first direction; and means for collecting the tissue bits drawn through said tube, said means for collecting being slidably disposed over a portion of said tube adjacent said first end, said collecting means being configured to retain the tissue bits therein yet permit communication of a vacuum in said chamber with said channel;

wherein the vacuum generated in said chamber draws the tissue bits through said channel and into said means for collecting, and the vacuum further draws said means for collecting away from said tube in said first direction as the tissue bits collect within said means for collecting to thereby permit continued communication of the vacuum with said channel, whereby the tissue bits are staged within said means for collecting in substantially the order in which they entered said channel.

6. The apparatus of claim 5 wherein said tissue collecting means includes a container having a plurality of apertures defined therethrough, said apertures being sized to permit communication of the vacuum therethrough yet retain excised tissue bits larger than a predetermined size therein.

7. The apparatus of claim 6 wherein said container includes an opening apart from said apertures and said tube includes an outer surface, said single opening being sized to receive said outer surface of said tube therein.

8. The apparatus of claim 7 wherein said single opening includes means for sealing said container to said outer surface of said tube, said sealing means permitting said container to slide along said outer surface of said tube as said container collects the tissue bits.

9. The apparatus of claim 8 further including:

a stop disposed adjacent said first end of said tube between said sealing means and said first end;

wherein said stop prevents said container from sliding along said outer surface of said tube when said container has been substantially filled with said tissue bits.

10. The apparatus of claim 9 wherein said sealing means includes a flexible ring and said stop includes a flange attached to said tube, and wherein said flexible ring is flexible enough to stretch over said flange to thereby permit said container to be loaded onto, and removed from, said tube.

11. The apparatus of claim 5 wherein said chamber includes an access entrance for accessing the contents of said chamber.

12. An apparatus for collecting and staging tissue bits excised from a patient comprising:

a chamber having a cover, said cover having a first surface facing said chamber, a first port connected to a source of vacuum for generating a vacuum in said chamber and a second port for receiving the excised tissue bits; and a tissue collection member disposed between said chamber and said cover, said tissue collection member, said chamber arid said cover being configured to permit relative rotation between said tissue collection member and one of said chamber and said cover, said tissue collection member including;

a third port axially aligned with said first port, wherein said cover, said tissue collection member and said chamber are in a sealing arrangement, thereby permitting communication of a vacuum in said first port with said chamber through said axially aligned first and third ports;

a number of elongated tubes each defining a channel therethrough for receiving the excised tissue bits, each of said number of tubes having a first end extending into said chamber in a first direction and a second end coterminous with said first surface of said cover; and a tissue collection container slidably disposed over a portion of at least one of said tubes adjacent said first end for collecting the tissue bits, said tissue collection container having apertures sized to retain the tissue bits therein yet permit communication of a vacuum in said chamber with said channel of said tube;

wherein rotation of said tissue collection member relative to one of said cover and said chamber axially aligns said second port with said second end of one of said elongated tubes so that a vacuum in said chamber draws the tissue bits through said second port, through said axially aligned tube and into said tissue collection container, and the vacuum further draws said collection container away from said tube in said first direction as the tissue bits collect within said collection container to thereby permit continued communication of the vacuum with said channel, whereby the tissue bits are staged within said collection container in substantially the order in which they entered said channel.

13. The apparatus of claim 12 wherein said number of tubes are radially disposed about the center of said tissue collection member.

14. The apparatus of claim 12 further including an operator controlled motor for rotating said tissue collection member relative to one of said chamber and said cover.

15. The apparatus of claim 14 wherein each of said tissue collection containers includes an opening apart from said apertures and a flexible ring adjacent said single opening for sealing said tissue collection container to one of said elongate tubes, yet permitting said tissue collection container to slide along said tube.

16. The apparatus of claim 15 wherein each of said elongated tubes further includes a flange adjacent said first end, said flange preventing movement of said flexible ring past said first end in said first direction.

17. The apparatus of claim 16 wherein said flexible ring is flexible enough to stretch over said flange to thereby permit said container to be loaded onto, and removed from, said tube.

18. The combination of:

a tissue morcellator for percutaneous tissue removal, said morcellator operable to excise tissue bits from a patient; and an apparatus for collecting and staging the excised tissue bits from said morcellator, said apparatus comprising:

a chamber having a first port connected to a source of vacuum for generating a vacuum in said chamber;

an elongated tube defining a channel therethrough for receiving the excised tissue bits, said tube having a first end extending into said chamber in a first direction; and a tissue collection container slidably disposed over a portion of said tube adjacent said first end, said tissue collection container having apertures sized retain the tissue bits therein yet permit communication of a vacuum in said chamber with said channel;

wherein the vacuum generated in said chamber draws the tissue bits through said channel and into said collection container, and the vacuum further draws said collection container away from said tube in said first direction as the tissue bits collect within said collection container to thereby permit continued communication of the vacuum with said channel, whereby the excised tissue bits are staged within said collection container in substantially the order in which they were excised.

19. The combination of claim 18 wherein said tissue collection container includes an opening apart from said apertures and a flexible ring adjacent said opening for sealing said tissue collection container to said elongated tube, yet permitting said tissue collection container to slide along said tube.

20. The combination of claim 19 wherein said elongated tube further includes a flange adjacent said first end, said flange preventing movement of said flexible ring past said first end in said first direction.

21. The combination of claim 20 wherein said flexible ring is flexible enough to stretch over said flange to thereby permit said container to be loaded onto, and removed from, said tube.

22. The combination of claim 21 further including a vacuum generator for providing said source of vacuum.

23. The combination of claim 22 further including a source of irrigation fluid connected to said tissue morcellator, wherein said collecting and staging apparatus receives said irrigation fluid in addition to the excised tissue bits.

24. The combination of claim 20 further including controller means for controlling the operation of said vacuum generator, said tissue morcellator and said irrigation fluid source.

* * * * *